(12) United States Patent
Adams

(10) Patent No.: US 6,533,755 B2
(45) Date of Patent: Mar. 18, 2003

(54) BALLOON WITH REVERSED CONES

(75) Inventor: Daniel O. Adams, Orono, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 39 days.

(21) Appl. No.: 09/775,034

(22) Filed: Feb. 1, 2001

(65) Prior Publication Data

US 2001/0011179 A1 Aug. 2, 2001

Related U.S. Application Data

(63) Continuation of application No. 09/398,344, filed on Sep. 17, 1999, now Pat. No. 6,221,042.

(51) Int. Cl.[7] ............................................. A61M 31/00
(52) U.S. Cl. ................................. 604/103.07; 606/194
(58) Field of Search ....................... 604/102.01, 103.07, 604/103.08, 103.13, 103.14, 915, 916; 606/192, 194, 108; 623/1.11

(56) References Cited

U.S. PATENT DOCUMENTS

| | | | |
|---|---|---|---|
| 3,726,283 A | 4/1973 | Dye et al. ............. 128/349 BV |
| 4,395,806 A | 8/1983 | Wonder et al. ......... 29/157.1 A |
| 4,606,347 A | 8/1986 | Fogarty et al. ............. 128/344 |
| 4,630,609 A | 12/1986 | Chin ........................... 128/344 |
| 4,763,654 A | 8/1988 | Jang ........................... 128/344 |
| 4,796,629 A | 1/1989 | Grayzel ..................... 128/344 |
| 4,921,478 A * | 5/1990 | Solano et al. ............. 604/53 |
| 4,941,877 A | 7/1990 | Montano, Jr. ................ 604/96 |
| 4,950,227 A | 8/1990 | Savin et al. .................... 604/8 |
| 4,994,072 A | 2/1991 | Bhate et al. ................ 606/194 |
| 5,041,089 A | 8/1991 | Mueller et al. ............... 604/96 |
| 5,041,125 A | 8/1991 | Montano, Jr. ............... 606/192 |
| 5,064,435 A | 11/1991 | Porter ........................... 623/12 |
| 5,071,407 A | 12/1991 | Termin et al. .............. 604/104 |
| 5,181,921 A | 1/1993 | Makita et al. .............. 606/195 |
| 5,221,261 A | 6/1993 | Termin et al. .............. 604/104 |
| 5,234,457 A | 8/1993 | Andersen .................... 606/198 |
| 5,254,091 A | 10/1993 | Aliahmad et al. ............ 604/96 |
| 5,338,298 A | 8/1994 | McIntyre ...................... 604/96 |
| 5,360,403 A | 11/1994 | Mische ....................... 604/101 |
| 5,370,691 A | 12/1994 | Samson ........................ 623/12 |
| 5,378,239 A | 1/1995 | Termin et al. .............. 604/104 |
| 5,401,257 A | 3/1995 | Chevalier, Jr. et al. ...... 604/256 |
| 5,464,450 A | 11/1995 | Buscemi et al. ............... 623/6 |
| 5,522,882 A | 6/1996 | Gaterud et al. ................ 623/1 |
| 5,653,691 A | 8/1997 | Rupp et al. ................... 604/96 |
| 5,662,607 A | 9/1997 | Booth et al. .................. 604/96 |
| 5,747,591 A * | 5/1998 | Chen et al. .................. 525/176 |
| 5,797,878 A | 8/1998 | Bleam ......................... 604/196 |
| 6,221,042 B1 | 4/2001 | Adams .................... 604/96.01 |

FOREIGN PATENT DOCUMENTS

| | | |
|---|---|---|
| EP | 0 937 482 A2 | 8/1999 |
| WO | WO 98/07390 A1 | 2/1998 |

* cited by examiner

Primary Examiner—Manuel Mendez
Assistant Examiner—Mark Han
(74) Attorney, Agent, or Firm—Crompton, Seager & Tufte, LLC

(57) ABSTRACT

A catheter assembly including a balloon which incorporates a reverse-cone design for improved stent delivery. The reverse-cone design provides an inflatable area which extends longitudinally over the balloon waist. When folded or deflated, the portions of the balloon extending over the waist in conjunction with the waists provide a bulky mass onto which a stent may be securely crimped without the use of additional structure under the balloon.

13 Claims, 1 Drawing Sheet

BALLOON WITH REVERSED CONES

This application is a continuation of application Ser. No. 09/398,344, filed Sep. 17, 1999 now U.S. Pat. No. 6,221,042.

FIELD OF THE INVENTION

The present invention pertains generally to a catheter balloon for medical dilation and stent delivery procedures. In particular, the present invention relates to the ability of a balloon, having a reversed-cone configuration, to secure a stent upon the balloon's body by selectively folding the balloon material forming the reversed-cones.

BACKGROUND OF THE INVENTION

Balloon catheters are used in the treatment of a variety of medical conditions. They are used extensively in conjunction with urinary, biliary, and vascular procedures. Among the more frequent uses for balloon catheters, however, is in vascular angioplasty of the peripheral and coronary arteries.

A vascular angioplasty procedure dilates the arteries that are obstructed (the stenosis), thereby improving blood flow through that region of the vasculature. In a typical angioplasty procedure, a balloon catheter is inserted percutaneously into the patient's arterial system. This percutaneous insertion is usually through the femoral artery. Once inside the patient's arterial system, the balloon catheter is advanced until the distal end of the catheter, where the balloon resides, is disposed adjacent to the obstruction. Once adjacent the stenosis, the balloon is inflated under fluid pressure to dilate the artery in the region of the stenosis.

Stents and stent delivery assemblies are utilized in conjunction with vascular angioplasty. Because dilated stenoses are known to reobstruct, a stent is often implanted to maintain the patency of the vessel.

A stent is a generally cylindrical prosthesis which is introduced, via a balloon catheter, into a lumen of a body vessel. The stent is positioned, and secured onto, the balloon in a configuration having a generally reduced diameter. Once the balloon catheter is positioned adjacent the desired location within the vasculature, the balloon is expanded. This balloon expansion subsequently causes the stent to increase its radial configuration from a reduced diameter (delivery diameter) to an expanded one (deployment diameter). In its expanded configuration, the stent supports and reinforces the vessel wall while maintaining the vessel in an open and unobstructed configuration.

The structure and functions of stents are well known. Stents used in conjunction with vascular angioplasty are shown in U.S. Pat. No. 5,064,435 to Porter; U.S. Pat. No. 5,071,407 to Termin et al.; U.S. Pat. No. 5,221,261 to Termin et al.; U.S. Pat. No. 5,234,457 to Anderson; U.S. Pat. No. 5,370,691 to Samson; U.S. Pat. No. 5,378,239 to Termin et al.; U.S. Pat. No. 5,401,257 to Chevalier, Jr. et al.; and U.S. Pat. No. 5,464,450 to Buschemi et al., all of which disclosures are incorporated herein by reference.

A distinguishable feature between stents is whether they are self-expanding or balloon expandable. Both self-expanding and balloon expandable stent are well known and widely available. The present invention is particularly concerned with enhanced stent securement and safer stent loading in the delivery and deployment of balloon expandable stents.

Balloon expandable stents are crimped to their reduced diameter about the balloon portion of the catheter assembly. The stents are gently crimped onto the balloon either by hand, or with a tool. Once the stent is mounted, the catheter system is ready for delivery. There are, however, two complications associated with crimping stents to balloon catheters: (1) excessive crimping may damage the stent, the balloon, or the inner lumen of the catheter; and (2) inadequate securement force results in failure of the stent to maintain its axial position during advancement within the human anatomy.

Most expandable stents have an minimum compression diameter. The minimum compression diameter is the smallest radial profile that a stent may be reduced to without causing damage to the stent. This damage often decreases the functionality and reliability of the stent's expansion, as well as its ability to maintain the patency of a vessel wall. Furthermore, the stent must be crimped over that portion of the balloon which is expandable in order to have the entire length of the stent expanded against the vessel wall on deployment. The expandable portion of present balloons typically have an insufficient outer diameter for direct attachment of a stent in the balloon's folded, deflated configuration. Therefore, crimping a stent on this section alone will cause the stent to bend undesirably or it will not be held adequately in axial position without artificially building-up the diameter under the balloon—or other means to create bulk for stent crimping.

Maintaining the stent's axial position during the advancement of the catheter to the deployment site is critical. If a stent is not adequately compressed upon the balloon, the stent may fail to secure properly to the catheter assembly and could be dislodged from the catheter during advancement within the human anatomy. It is important, therefore, that the location where the stent is to be secured have an outer diameter (in the folded deflated configuration) greater than or equal to the stent's minimum compression diameter so that it may be firmly secured to the balloon catheter assembly. There are a number of devices used for maintaining a stent's axial securement about the balloon catheter.

U.S. Pat. No. 4,950,227 to Savin et al., relates to a stent delivery system in which a sleeve overlaps the distal or proximal margin (or both) of the stent during delivery. This sleeve maintains the stent's axial position during the advancement of the catheter assembly to the deployment site. To deploy the stent, the stent margins are freed of the protective sleeve(s) and the sleeve then collapses toward the delivery catheter for removal.

PCT International Application No. WO 98/07390, published Feb. 26, 1998, discloses a delivery catheter using mounting bodies that have outer diameters exceeding the minimum compression diameter of a stent. The outer diameters of the mounting bodies are also circumferentially larger than the deflated balloon diameter. Therefore, the stent is crimped securely upon the mounting bodies in order to insure axial position during the catheter's advancement. The use of mounting bodies, however, affects the flexibility of the inner shaft within the balloon which is not desired. This application is incorporated herein by reference.

SUMMARY OF THE INVENTION

This invention is generally directed to a catheter apparatus suitable for performing angioplasty and for delivery of stents to body cavities. In particular, this invention is directed to a balloon catheter having a balloon with reverse-cone configuration. This reverse-cone configuration allows stents, or other implantable devices, to securely, yet reversibly, attach directly to the body of a catheter balloon without the need, expense, or detrimental impact on performance due to additional apparatus such as mounting bodies.

An additional embodiment of the invention is a means for selectively folding the balloon material in order to secure a stent upon a balloon that is not shaped with reverse cones. The embodiment is particularly directed to improved arrangements between balloon catheters known in the art and a stent. This embodiment teaches a means for reversibly attaching and securing a stent to a balloon catheter without the need for additional fastening devices. In particular, this embodiment illustrates the creation of pleated bodies that act as bulky masses for which to attach a stent. A further embodiment of the invention is the manipulation of balloon material densities, in either the reverse-coned configuration, or in those balloons known in the art, to obtain a desired outer diameter for the pleated bodies.

The present invention is also directed to a method for formation of the reverse-cone balloon. In particular, the methods used to convert a balloon known in the art into a balloon having a reverse-cone configuration.

DETAILED DESCRIPTION

Figure 1:
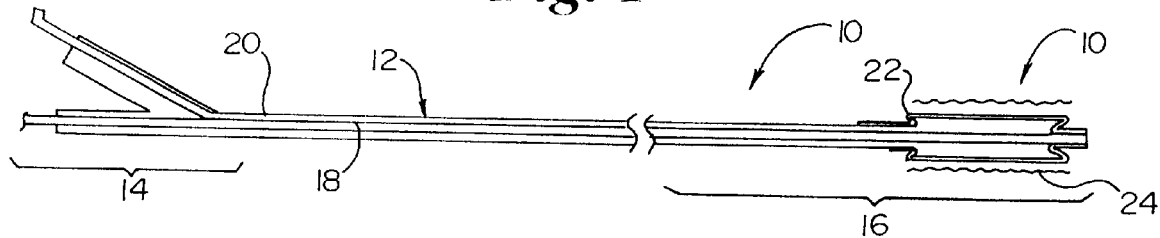
FIG. 1 is a side view of a balloon catheter assembly.

FIG. 1 is a side view of a balloon catheter assembly 10. The balloon catheter assembly 10 generally comprises a catheter shaft 12 with a proximal end 14 and a distal end 16. The catheter shaft 12 preferably comprises at least two lumens extending within the catheter shaft 12. At least one lumen is preferably a guidewire lumen 18. The guidewire lumen 18 may extend the entire length of the catheter shaft 12 (e.g. over-the-wire catheter), or it may extend along a portion of the catheter shaft 12, wherein it exits the catheter shaft 12 at the distal end 16 (e.g. single operator exchange catheter).

Another lumen necessary to enable the invention is an inflation lumen 20. The inflation lumen 20 allows fluid communication between an inflation source and an inflatable balloon 22. In general, the proximal end of the inflation lumen 20 is attached to the inflation source while the distal end of the inflation lumen 20 is in fluid communication with the interior of the inflatable balloon 22. In a preferred embodiment, the proximal end of the catheter shaft 14 has a manifold. One branch of this manifold may connect the inflation source to the inflation lumen 20. Therefore, this branch may be used to inflate and deflate the inflatable balloon 22 which the inflation lumen 20 is fluidly connected. In preferred embodiments, the shaft is a co-axial design, with an inner tubular member disposed co-axially within an outer tubular member as depicted in FIG. 1. The guidewire lumen 18 is within the inner tubular member while the inflation lumen is formed by the annular space between the inner and outer tubular members. Alternatively, a multilumen single shaft could be utilized.

The distal end of the catheter shaft 16 comprises the tip portion of the balloon catheter assembly 10. At the distal end of the tip portion is preferably a soft distal tip. This soft distal tip generally comprises a polymeric material to improve tracking through arterial bends.

Proximate the tip portion of the catheter shaft is the inflatable balloon 22. In preferred embodiments the proximal end of the balloon is hermetically affixed to the outer tubular member near its distal end, while the distal end of the balloon is hermetically affixed to the inner tubular member proximate its distal end which extends distally from the outer tubular member. Surrounding the inflatable balloon 22 is a device 24 for maintaining the patency of a vessel wall. This device 24 is generally expandable with the inflatable balloon 22. A balloon expandable stent is an exemplary example of such a device.

The balloon catheter assembly 10 of FIG. 1 may be used in the treatment of a variety of medical conditions. Specifically, the balloon catheter assembly 10 may be used in conjunction with urinary, biliary, and vascular procedures. Although other procedures may be performed, the present invention will notably be discussed in relation to vascular angioplasty of the peripheral and coronary arteries.

Figure 2:
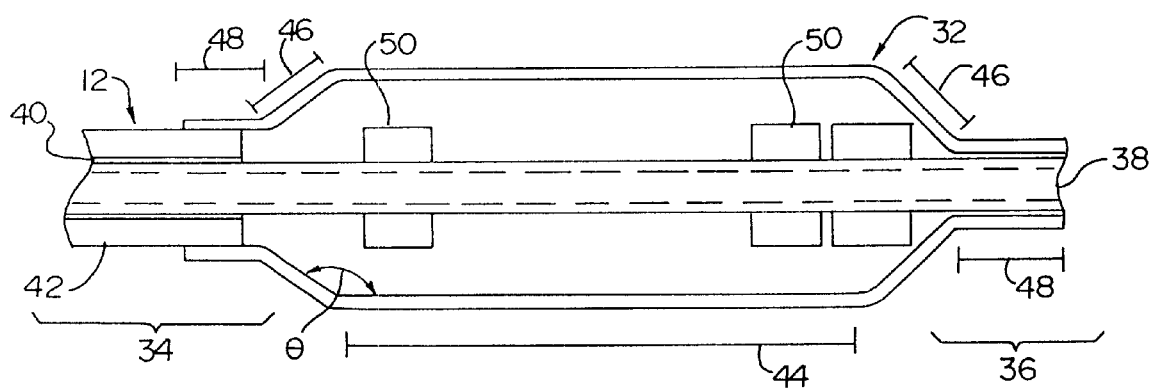
FIG. 2 is a cross-sectional view of a balloon known in the prior art having mounting bodies placed over the inner lumen.

FIG. 2 is a cross-sectional side view of the distal tip portion of a balloon known in the art. Specifically, FIG. 2 illustrates an expanded inflatable balloon 32 wherein the distal tip portion of the catheter shaft includes a proximal end 34 and a distal end 36. Throughout the distal tip portion is an inner lumen 38 for receiving a guidewire. At the proximal end of the distal tip portion 34 is an inflation lumen 40 extending alongside the inner lumen 38. The inflation lumen 40 is in fluid communication with an inflation source that controls the inflationary state of the balloon 32. The inflation lumen 40 connects to the inflatable balloon 32 at the end of the outer tubular member 42. There are many means for fluidly connecting the inflation lumen 40 to the inflatable balloon 32. The means depicted is not meant to be limiting, but purely illustrative. The inflatable balloon 32 of FIG. 2 includes at least three distinct regions. These regions, although distinguished, remain a part of one contiguous balloon. The regions are distinguished only to illustrate the design features of the balloon.

The first region is the centermost section of the balloon 44. The centermost section 44 is the portion of the balloon which, when inflated, runs parallel with, and engages the vessel wall or inner diameter of a stent. The centermost section 44 comprises the majority of the inflatable balloon 32. The length of the centermost section of balloons known in the art 44 typically end short of reaching the waist regions of the balloon 48.

The second regions are the cone sections of the balloon 46. The cone sections 46 are the portions of the balloon which reduce the diameter of the balloon so that it can be connected to the shaft 12.

The third regions are the waists of the balloon 48. These are the sections of the balloon which run parallel with, overlap, and are adhered to the catheter shaft 12. The waists of the balloon 48 are hermetically sealed to prevent inflation fluid from escaping. An adhesive preferably seals the waist sections of the balloon 48 to the outer tubular member 42 at the balloon's proximal end and the outer diameter of the inner lumen 38 at the balloon's distal end. Other suitable methods for sealing the waists 48 include the application of heat, polymer overlay, or the like. As illustrated in FIG. 2, the balloon includes a single centermost section, a proximal cone section, a distal cone section, a proximal waist, and a distal waist.

The cone sections of the balloon, on either end, reduce the diameter to that of the waist and form an angle (θ) or conical angle as defined in FIG. 2 relative to the centermost section 44. In a cross-section of a balloon, as seen in FIG. 2, the interior angle (inside the balloon) formed between the centermost section 44 and the conical section 46 is the conical angle, theta, of the balloon 32.

The prior art balloon 32 in FIG. 2 comprises a conical angle, theta, of approximately 120 degrees. Most balloons known in the art comprise, as defined herein, a conical angle, theta, of greater than 90 degrees. With this conical angle, the cone sections 46 of the balloon must taper toward the ends of the catheter shaft 12 from the centermost section to the waists, as depicted in FIG. 2.

Expandable stents, and other implantable devices, must be positively secured to the catheter assembly. Most expandable stents, however, have a minimum compression diameter. The minimum compression diameter is the smallest radial profile that a stent may be reduced to without damaging the stent or its mechanical properties. Over compression could decrease the functionality and reliability of the stent's expansion, as well as its ability to maintain the patency of a vessel wall. Additionally, if a stent is over-compressed, the stent may fail to secure properly to the catheter assembly. This may cause the stent to move axially on the balloon. It is important, therefore, that the location where the stent is to be secured have an effective bulk outer diameter greater than or equal to the stent's minimum compression diameter.

Further, the stent must be mounted over its length onto an expandable portion of the balloon. This is necessary so that the entire stent is expanded during delivery and is in contact over its length with the wall of the vessel. Thus, a stent mounted on the balloon of FIG. 2 must not extend on either end beyond the centermost section or expandable portion.

Unique to the distal tip portion of FIG. 2 is the inclusion of mounting bodies 50. Mounting bodies 50 are preferably ring-like or compressible cylindrical elements that are placed over the inner lumen 38 and under the centermost portion 44 of the balloon. The importance of these mounting bodies 50 is that they extend radially from the inner lumen 38 to provide a surface area of adequate diameter for mounting the stent. A stent, therefore, may be securely crimped upon the mounting bodies 50 without exceeding the stent's minimum compression diameter. The present invention is directed to a balloon design which eliminates the need for mounting bodies 50.

Figure 3:
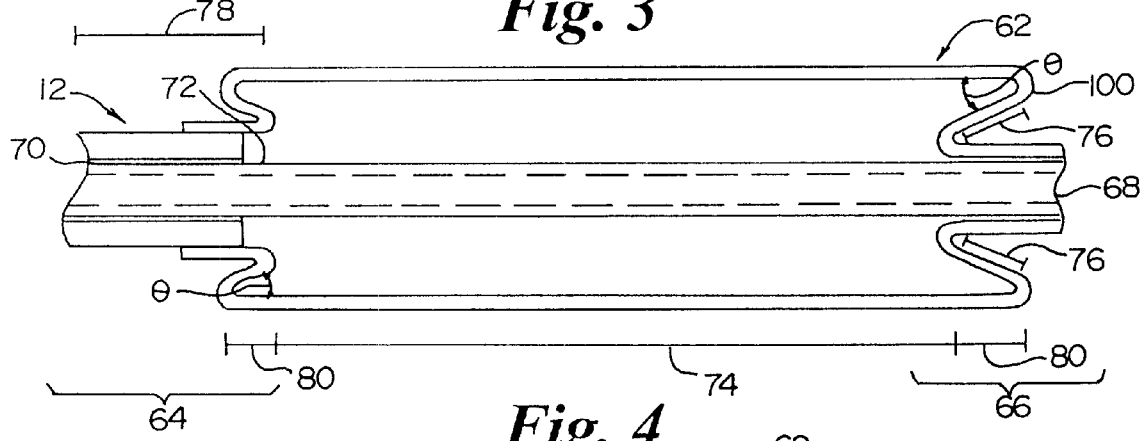
FIG. 3 is a cross-sectional view of a preferred catheter balloon in an expanded state having a reverse-coned configuration.

Now referring to FIG. 3, a cross-sectional view of a preferred distal tip portion of a balloon catheter assembly of the present invention with the inflatable balloon 62 in an expanded state is depicted. The inflated balloon 62 in FIG. 3 illustrates a preferred reverse-cone balloon. The distal tip portion of the preferred reverse-cone balloon comprises a proximal end 64 and a distal end 66 similar to those known in the art. Throughout the distal tip portion is an inner lumen 68 for preferably receiving a guidewire. At the proximal end of the distal tip portion 64 is an inflation lumen 70 formed in the annular space alongside the inner lumen 68. The inflation lumen 70 is in fluid communication with an inflation source that controls the inflation state of the reverse-cone balloon 62. The inflation lumen 70 connects to the reverse-cone balloon 62 at an opening 72. There are many means for fluidly connecting the inflation lumen 70 to the reverse-cone balloon 62. The means depicted is not meant to be limiting, but purely illustrative.

Similar to balloons known in the art 32, the preferred reverse-cone balloon 62 comprises three distinct regions. Unlike balloons known in the art 32, such as FIG. 2, the preferred reverse-cone balloon 62 has a unique conical angle θ to form a balloon of unique shape and structure which functions to provide bulk for crimping a stent onto the balloon material without use of mounting bodies.

The centermost section 74 of the preferred reverse-coned balloon 62 extends lengthwise over the proximal and distal waist of the balloon 78 forming extended portions 80. The extended portions 80 of the centermost section 74 of the preferred reverse-cone balloon 62 allows the balloon material to rest upon the waist portion of the balloon 78 when in a deflated state. These added bulk portions, over the waists of the balloon, form pleated bodies 100. Pleated bodies 100 create an effective bulk outer diameter greater than or equal to a stent's minimum compression diameter. Therefore, these pleated bodies 100 aid in stent crimping.

Because the centermost section 74 of the reverse-coned balloon 62 extends lengthwise 80 over the waist of the balloon 78, the conical angle, theta, of the balloon is preferably less than 90 degrees. In order to form the waist of the balloon 78 under the extended centermost section 80, the cone section of the reverse-cone balloon 76 needs to be directed inward toward the axial center of the balloon. When the cone section 76 is directed inward, the conical angle, theta, must be less than 90 degrees. FIG. 3 illustrates the cone section 76 directed inward toward the center of the reverse-coned balloon 62 and toward the catheter shaft 12. FIG. 3 additionally illustrates the corresponding conical angle, theta, (approximately 45 degrees) needed to obtain the necessary pitch for the cone section 76. The cross-section of FIG. 3 further illustrates that a conical angle, theta, of less than 90 degrees in the inflated state, creates an S-shaped configuration at the ends of the preferred reverse-cone balloon 62.

Figure 4:
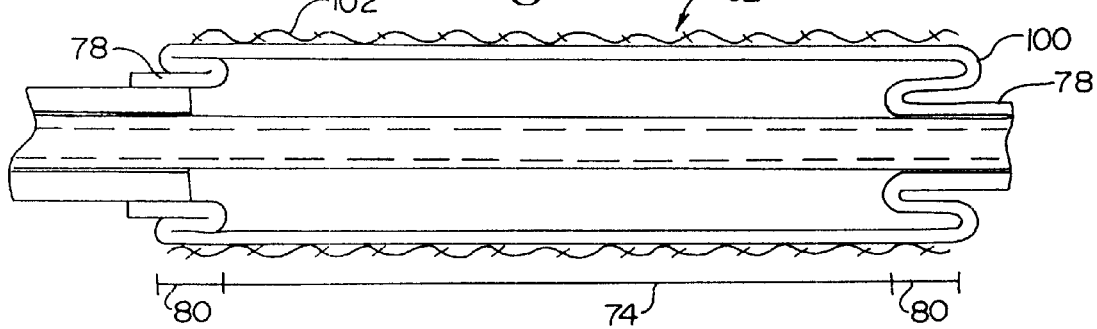
FIG. 4 is a cross-sectional view of a preferred catheter balloon configuration in a deflated state having a stent securely attached to the catheter balloon's body.

When the reverse-cone balloon 62 is deflated, as seen in FIG. 4, the extended balloon material 80 of the centermost section 74 folds forming multi-layered pleated bodies 100 over the waist of the balloon 78. These pleated bodies 100 are formed at both ends of the reverse-cone balloon 62. This added bulk of the pleated bodies 100 over the waist portion of the balloon 78 yields a substantially increased circumferential diameter at these locations when the balloon is deflated. This increased circumferential diameter is selected to be greater than or equal to the minimum compression diameter of most stents. A stent 102, therefore, may be safely secured upon the pleated bodies 100 and waist of a deflated reverse-coned balloon 62 because the pleated bodies 100 extend farther radially than a typical stent's minimum compression diameter. FIG. 4 illustrates a stent 102 securely attached onto the pleated bodies 100 positioned over the waist of the balloon 78.

In a procedure, the stent 102 is positioned over the reverse-coned balloon 62 where it is gently crimped onto the balloon material, specifically onto the pleated bodies 100 as folded over the waists. This crimping may be performed either by hand or with a crimping tool or the like. When the stent 102 is securely fastened to the pleated bodies 100, the stent 102 is ready for delivery within the vasculature.

When the preferred reverse-cone balloon 62 is positioned over the site for stent deployment, the balloon is radially expanded. The radial expansion of the balloon unfolds the pleated bodies 100, forming the elongated centermost section 74. The reverse-cone balloon 62 then expands the stent 102 until the stent 102 reaches the vessel wall. In this position, the stent 102 is fully deployed and capable of maintaining the patency of the vessel wall. Finally, the reverse-cone balloon 62 is deflated and removed from the vasculature.

The pleated bodies of the reverse-cone balloon 100 may be replicated in other shaped balloons. In an additional embodiment, the pleated bodies 100 may be formed in inflatable balloons 32 with conical angle, theta, of 90 degrees or more (see FIG. 2).

These inflatable balloons 32 have all three distinct regions as described infra. The centermost sections 44 all run longitudinally with the catheter shaft. The cone section 46 is pitched according to the conical angle, theta. With balloons having conical angle, theta, of 90 degrees or more, the cone section 46 is generally pitched toward the ends of the catheter shaft 12.

When forming pleated bodies 100 in these balloon configurations, the cone section 46 must be of sufficient length as to allow the balloon material to be folded and drawn over the waists of the balloon 48. The degree to which this may be accomplished will be a function of the centermost section diameter relative to the waist diameter. The added bulk of the pleated bodies 100 over the waist portion of the balloon 48 increases the circumferential diameter at these locations. This increased circumferential diameter is preferably greater than the minimum compression diameter of most balloon expandable stents. A stent 102, therefore, may be safely secured upon the pleated bodies 100 of a deflated balloon having a conical angle, theta, of 90 degrees or more because the pleated bodies 100 extend farther radially than a typical stent's minimum compression diameter.

Referring to FIG. 3, the folded regions forming the pleated bodies 100 of the reverse-coned balloon are generally stiffer than a conventional balloon 32 (see FIG. 2). These folded regions are additionally generally short in length. These attributes aid the catheter in tracking through the tortuous bends within the human anatomy.

The balloon material in any of the catheter balloon embodiments discussed vary depending upon the compliance of the balloon material desired. In general, the balloon material desired for the embodiments is either a polyether block amide (PEBAX), or polyethylene. When a compliant balloon material is desired, low pressure, relatively soft or flexible polymeric materials such as thermoplastic polymers, thermoplastic elastomers, polyethylene (high density, low density, intermediate density, linear low density), various co-polymers and blends of polyethylene, ionomers, polyesters, polyurethanes, polycarbonates, polyamides, poly-vinyl chloride, acrylonitrile-butadiene-styrene copolymers, polyether-polyester copolymers, and polyether-polyamide copolymers are preferred. When a non-compliant balloon material is desired, materials having relatively rigid properties such as poly(ethylene terphthalate), polyimide, thermoplastic polyimide, polyamides, polyesters, polycarbonates, polyphenylene sulfides, polypropylene and rigid polyurethanes are desired.

Variations in the balloon thickness may be made to any of the embodiments discussed infra. Reasons for varying the balloon thickness include, among others, to facilitate the creation of the pleating bodies 100 and/or to increase the circumferential diameter that the pleating bodies 100 yield, and to achieve various balloon pressure ratings. Material may be added, removed, or a combination thereof in order to achieve proper folding. Areas of particular interest for balloon thickness augmentation are the extended regions of the centermost section and the cone sections of the balloon.

To make the reverse-cone embodiment, an inflatable balloon known in the art 32 (such as in FIG. 2) is molded in a conventional manner. A secondary process is then initiated to reform the balloon into a reverse-coned shape. The conventional balloon is first placed within the centermost section of a mold having a reverse-coned shape. The balloon is then low pressure inflated in the centermost section of the mold over a mandrel. The cone ends of the mold are then advanced to close the mold. The balloon is subsequently placed at a higher pressure and the mold heated to a temperature sufficient to cause a permanent set to keep the cones reversed after molding. Heating may be accomplished by any method currently known in the art, including but not limited to, direct current (DC), radiofrequency (RF), inductance, and infrared radiation (IR). After the reverse-cones are formed, the balloon is allowed to cool. Cooling generally occurs by placing the balloon under air pressure while within the mold or placed within a cold water bath. Alternatively, the balloon could be blown conventionally and the cones reversed when bonded to the inner lumen and the outer tubular member with no secondary heat forming.

Once the reverse-coned balloon is formed, the balloon is folded to form the pleated bodies 100. The pleated bodies 100 are formed by positioning the deflated reverse-cones over the waists of the balloon 48. This may be accomplished by folding and drawing the deflated balloon material over the waists of the balloon 48. The degree of folding necessary depends upon the minimum compression diameter of the stent to be used. The folding of the pleated bodies 100 must allow for a circumferential diameter greater than that of the stent's minimum compression diameter. Finally, a stent 102 is secured upon the pleated bodies 100.

Numerous characteristics and advantages of the invention covered by this document have been set forth in the foregoing description. It will be understood, however, that this disclosure is, in many aspects, only illustrative. Changes may be made in details, particularly in matters of shape, size, and arrangement of parts without exceeding the scope of the invention. The invention's scope is defined, of course, in the language in which the appended claims are expressed.

What is claimed is:

1. A stent delivery assembly comprising:

a catheter shaft having a proximal end and a distal end, wherein an inflation lumen extends therethrough;

an inflatable member having a proximal end, a distal end and an expandable region therebetween, the expandable region of the inflatable member being in fluid communication with the inflation lumen, further wherein the proximal end of the inflatable member is affixed to the catheter shaft at a first attachment site and the distal end of the inflatable member is attached to the catheter shaft at a second attachment site, and further wherein, prior to inflation, a portion of the expandable region of the inflatable member extends over at least a portion of both the first and second attachment sites; and an expandable stent placed upon at least a section of the expandable region of the inflatable member that extends over at least a portion of both the first and second attachment sites.

2. The stent delivery assembly of claim 1, wherein the catheter shaft includes an outer tubular member having a distal end with the first attachment site proximate the distal end of the outer tubular member and an inner tubular member having a portion coaxially disposed within the outer tubular member including a distal end extending distally beyond the outer tubular member with the second attachment site proximate the distal end of the inner tubular member.

3. A catheter balloon assembly comprising:

an inflatable member having a proximal end, a distal end and an expandable segment therebetween, wherein the proximal end of the inflatable member is affixed to a catheter shaft at a first attachment site and the distal end of the inflatable member is attached to the catheter shaft at a second attachment site, wherein, prior to inflation, a portion of the expandable segment of the inflatable member extends over at least a portion of both the first and second attachment sites, and further wherein, the catheter shaft includes an outer tubular member having a distal end with the first attachment site proximate the distal end of the outer tubular member and an inner tubular member having a portion coaxially disposed within the outer tubular member including a distal end extending distally beyond the outer tubular member with the second attachment site proximate the distal end of the inner tubular member.

4. The catheter balloon assembly of claim 3, wherein the catheter balloon comprises a cylindrical body comprising a polymeric balloon material.

5. The catheter balloon assembly of claim 4, wherein the polymeric balloon material is selected from the group consisting of thermoplastic polymers, thermoplastic elastomers, polyethylene (high density, low density, intermediate density, linear low density), various co-polymers and blends of polyethylene, PEBAX, ionomers, polyesters, polyurethanes, polycarbonates, polyamides, poly-vinyl chloride, acrylonitrile-butadiene-styrene copolymers, polyether-polyester copolymers, and polyetherpolyamide copolymers.

6. The catheter balloon assembly of claim 3, wherein the catheter balloon comprises a non-compliant polymeric balloon material.

7. The catheter balloon assembly of claim 6, wherein the non-compliant polymeric balloon material is selected from the group consisting of poly(ethylene terphthalate), polyimide, thermoplastic polyimide, polyamides, polyesters, polycarbonates, polyphenylene sulfides, polypropylene and rigid polyurethanes.

8. A catheter balloon assembly comprising:

a balloon member having a proximal end and a distal end, wherein the proximal end of the balloon member is affixed to a catheter shaft at a first attachment site and the distal end of the balloon member is affixed to the catheter shaft at a second attachment site, the balloon member further being expandable from a first diameter to a second diameter;

a proximal and a distal cone section comprising the portions of the balloon member extending over at least a portion of the first and second attachment sites, wherein the proximal and distal cone sections include an angle of 90 degrees or less defined by the interior angle within the proximal and distal cone sections when the balloon member is at said first diameter.

9. The catheter balloon assembly of claim 8, wherein the catheter shaft includes an outer tubular member having a distal end with the first attachment site proximate the distal end of the outer tubular member and an inner tubular member having a portion coaxially disposed within the outer tubular member including a distal end extending distally beyond the outer tubular member with the second attachment site proximate the distal end of the inner tubular member.

10. The catheter balloon assembly of claim 8, wherein the angles of the proximal and distal cone sections are less than or equal to 90 degrees when the balloon member is expanded to the second diameter.

11. The catheter balloon assembly of claim 8, wherein the angles of the proximal and distal cone sections are greater than 90 degrees when the balloon member is expanded to the second diameter.

12. A stent delivery catheter comprising:

a first tubular member having a lumen extending the length therein;

a second tubular member coaxially disposed within at least a portion of the first tubular member with a distal segment extending distally beyond a distal end of the first tubular member;

a balloon having a proximal end, a distal end and an expandable region therebetween, the expandable region of the balloon being in fluid communication with the lumen of the first tubular member, further wherein the proximal end of the balloon is affixed to the first tubular member at a first attachment site and the distal end of the balloon is affixed to the distal segment of the second tubular member at a second attachment site, and further wherein at least a portion of the expandable region is folded over at least a portion of both the first and second attachment sites; and an expandable stent placed upon at least a section of the portions of the expandable region being folded over at least a portion of the first and second attachment sites.

13. A catheter balloon assembly comprising:

an inflatable member having a proximal end, a distal end and an expandable segment therebetween, wherein the proximal end of the inflatable member is affixed to a catheter shaft at a first attachment site and the distal end of the inflatable member is attached to the catheter shaft at a second attachment site, wherein, prior to inflation, at least three layers of the balloon material overlay the shaft over a portion of each of the first and second attachment sites, and further wherein, the catheter shaft includes an outer tubular member having a distal end with the first attachment site proximate the distal end of the outer tubular member and an inner tubular member having a portion coaxially disposed within the outer tubular member including a distal end extending distally beyond the outer tubular member with the second attachment site proximate the distal end of the inner tubular member.

* * * * *